(12) United States Patent
Becker et al.

(10) Patent No.: US 9,760,830 B2
(45) Date of Patent: Sep. 12, 2017

(54) CONTROL METHOD AND CONTROL SYSTEM

(71) Applicant: Siemens Aktiengesellschaft, Munich (DE)

(72) Inventors: Hans-Christoph Becker, Starnberg (DE); Ute Feuerlein, Erlangen (DE); Michael Scheuering, Nuremberg (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 436 days.

(21) Appl. No.: 14/368,684

(22) PCT Filed: Dec. 11, 2012

(86) PCT No.: PCT/EP2012/075104
§ 371 (c)(1),
(2) Date: Jun. 25, 2014

(87) PCT Pub. No.: WO2013/098074
PCT Pub. Date: Jul. 4, 2013

(65) Prior Publication Data
US 2015/0039553 A1   Feb. 5, 2015

(30) Foreign Application Priority Data

Dec. 28, 2011   (DE) .................. 10 2011 090 047

(51) Int. Cl.
*G06K 9/00* (2006.01)
*G06N 5/04* (2006.01)
(Continued)

(52) U.S. Cl.
CPC ............... *G06N 5/04* (2013.01); *A61B 6/481* (2013.01); *A61B 6/54* (2013.01); *G05B 15/02* (2013.01);
(Continued)

(58) Field of Classification Search
None
See application file for complete search history.

(56) References Cited

U.S. PATENT DOCUMENTS

| 5,840,026 A | 11/1998 | Uber, III et al. |
| 6,385,483 B1 | 5/2002 | Uber, III et al. |

(Continued)

FOREIGN PATENT DOCUMENTS

| CN | 101185591 A | 5/2008 |
| CN | 101443813 A | 5/2009 |

(Continued)

OTHER PUBLICATIONS

International Search Report PCT/ISA/210 for International Application No. PCT/EP2012/075104 Dated Nov. 21, 2013.
(Continued)

*Primary Examiner* — Soo Park
(74) *Attorney, Agent, or Firm* — Harness, Dickey & Pierce, P.L.C.

(57) ABSTRACT

A control method is disclosed for determining a quality indicator of medical technology recording results data from a tomography scan of an examination structure, which scan is supported by a contrast agent, by way of a tomography system. According to an embodiment of the invention, at least one control parameter value is automatically derived from the recording results data in respect of a contrast agent image region during and/or directly after the tomography scan, which value represents a quality of the recording results data in the contrast agent image region. A control system for such a determination is also disclosed.

20 Claims, 6 Drawing Sheets

(51) Int. Cl.
*A61B 6/00* (2006.01)
*G06T 11/00* (2006.01)
*G06T 7/00* (2017.01)
*G05B 15/02* (2006.01)
*G06F 19/00* (2011.01)
*A61B 6/03* (2006.01)
*A61B 5/055* (2006.01)
*A61M 5/00* (2006.01)

(52) U.S. Cl.
CPC ............ *G06F 19/32* (2013.01); *G06T 7/0012* (2013.01); *G06T 11/005* (2013.01); *A61B 5/055* (2013.01); *A61B 6/032* (2013.01); *A61B 6/037* (2013.01); *A61B 6/5205* (2013.01); *A61M 5/007* (2013.01); *G06T 2207/30168* (2013.01)

(56) References Cited

U.S. PATENT DOCUMENTS

| | | | |
|---|---|---|---|
| 7,672,711 | B2 | 3/2010 | Haras |
| 8,571,290 | B2 * | 10/2013 | Wang .................. G06T 5/00 382/131 |
| 2001/0056233 | A1 | 12/2001 | Uber et al. |
| 2003/0050556 | A1 | 3/2003 | Uber et al. |
| 2004/0162488 | A1 | 8/2004 | Uber et al. |
| 2006/0193437 | A1 * | 8/2006 | Boeing .................. A61B 6/032 378/115 |
| 2007/0066892 | A1 | 3/2007 | Haras et al. |
| 2007/0076928 | A1 * | 4/2007 | Claus .................... G06T 11/006 382/128 |
| 2007/0225601 | A1 | 9/2007 | Uber et al. |
| 2007/0282199 | A1 | 12/2007 | Uber et al. |
| 2008/0027309 | A1 | 1/2008 | Hempel et al. |
| 2008/0045834 | A1 | 2/2008 | Uber et al. |
| 2008/0119715 | A1 | 5/2008 | Gonzalez Molezzi et al. |
| 2008/0219530 | A1 | 9/2008 | Levanon et al. |
| 2008/0226147 | A1 | 9/2008 | Hargrove et al. |
| 2008/0226148 | A1 | 9/2008 | Gu et al. |
| 2008/0253634 | A1 | 10/2008 | Hay et al. |
| 2009/0147001 | A1 | 6/2009 | Buelow et al. |
| 2011/0110572 | A1 * | 5/2011 | Guehring ............. A61B 6/5258 382/131 |
| 2011/0208046 | A1 | 8/2011 | Gonzalez Molezzi et al. |
| 2011/0313287 | A1 | 12/2011 | Komatsu et al. |
| 2012/0051614 | A1 | 3/2012 | Olszewski et al. |
| 2015/0039553 | A1 | 2/2015 | Becker et al. |

FOREIGN PATENT DOCUMENTS

| | | |
|---|---|---|
| DE | 102005041626 A1 | 3/2007 |
| DE | 102006032991 A1 | 1/2008 |
| EP | 0702966 A2 | 3/1996 |
| JP | 2008126072 A | 6/2008 |
| WO | WO 0108552 A1 | 2/2001 |
| WO | WO-2007039838 A2 | 4/2007 |
| WO | WO 2007132421 A1 | 11/2007 |
| WO | WO-2008050222 A2 | 5/2008 |
| WO | WO 2010101184 A1 | 9/2010 |
| WO | WO-2010128412 A1 | 11/2010 |
| WO | WO 2013098074 A2 | 7/2013 |

OTHER PUBLICATIONS

Written Opinion of the International Searching Authority PCT/ISA/237 for International Application No. PCT/EP2012/075104 dated Nov. 21, 2013.
German Office Action dated Dec. 12, 2012.
Y. Zheng et al. "Constrained Marginal Space Learning for Efficient 3D Anatomical Structure Detection in Medical Images" Integrated Data Systems Department.
Chinese Office Action and English translation thereof dated Apr. 25, 2016.
Korean Office Action and English translation thereof dated Aug. 12, 2015.
German Office Action dated Oct. 12, 2012.
Korean Office Action and English translation thereof dated Jul. 14, 2016.
Chinese Office Action and English translation thereof dated Sep. 28, 2015.
Notice of Allowance for Corresponding Korean Patent Application No. 10-2014-7021005 dated May 29, 2017.
Office Action for Corresponding Chinese Patent Application No. 201280070301.0 dated May 25, 2017 and English translation thereof.

* cited by examiner

CONTROL METHOD AND CONTROL SYSTEM

PRIORITY STATEMENT

This application is the national phase under 35 U.S.C. §371 of PCT International Application No. PCT/EP2012/075104 which has an International filing date of Dec. 11, 2012, which designated the United States of America, and which claims priority to German patent application number DE 102011090047.0 filed Dec. 28, 2011, the entire contents of each of which are hereby incorporated herein by reference.

FIELD

At least one embodiment of the invention generally relates to a control method for determining a quality indicator of medical technology recording results data from a contrast-agent-assisted tomography scan of an examination structure by means of a tomography system. It also relates to a control system for determining such a quality indicator.

BACKGROUND

Contrast-agent-assisted tomography scans are now an indispensible part of medical imaging technology. Around 80% of all computed tomography examinations (and also a considerable proportion of magnetic resonance tomography examinations) are currently carried out in this way using contrast agents. This means that in addition to the parameter value settings of the respective image recording system other important parameter values for administering the respective contrast agent must be set correctly in order to achieve a sufficient image quality of the captured tomography image data. Medical technology imaging systems or tomography systems principally include all automatic or semi-automatic image recording systems such as ultrasound, computed tomography systems (CT), magnetic resonance tomography systems (MR) and special tomography systems which are designed specifically for contrast-agent-based tomography recordings—for instance SPECT (Single Photon Emission Computed Tomography) or PET (Positron Emission Tomography).

Contrast agents are generally defined as those agents which improve the depiction of structures and functions of the body in imaging procedures such as X-ray diagnostics, magnetic resonance tomography (MRT) and sonography (ultrasound). The effect of contrast agents is to modify the signal which is registered in the respective examination. The purpose of using them is to obtain additional information during the examination. For example, in radiography frequent use is made of contrast agents which absorb the X-rays more strongly than normal soft tissue. Usually no blood vessels are visible on an X-ray image. If for example a solution containing iodine is injected as a contrast agent, the vessels which the solution reaches throw X-ray shadows and in this way become visible. Normally contrast agents are differentiated from so-called tracers. These relate to an artificial, often radioactively marked substance which is internal or external to the body, and which after introduction into the living body participates in the metabolic process and in addition permits or facilitates a wide variety of examinations. In the context of the present application agents conventionally defined as contrast agents as well as tracers are both referred to generally as "contrast agents".

Contrast agents can be administered in pure form or mixed with other, thinning agents. Thus it is for example usual to admix a dose of a particular contrast agent with a particular quantity of saline solution or to administer these two agents simultaneously.

In medical technology imaging an accumulation of contrast agent in the examination object (normally therefore a patient) which is both sufficient in quantity and also evenly distributed is necessary, in order subsequently on the basis of the captured recording results data to provide a basis for a diagnosis by a physician. Also, to be able to evaluate the recording results data in a so-called postprocessing application, in other words an automatic evaluation device, a particular image quality must be achieved, since otherwise the necessary algorithms, for example during segmentation in postprocessing, supply false or inadequate results.

The reasons for insufficient contrast may be many and varied. For example they include:

Incorrect timing of the imaging scanner after an injection of contrast agent, for example in stenoses: for example in an intravenous injection of a contrast agent the distribution of the contrast agent in the vascular system may be delayed by a vascular stenosis, in other words a narrowing, for instance in the carotid artery, so that for example sufficient contrast agent has not yet arrived in the brain, although this could have been reckoned with.

Scanning does not last long enough, as may occur for example in so-called flash scans. Flash scan means a tomography scan which is performed very quickly, in particular with a fast feed of the patient table.

An inadvertent injection of pure saline solution instead of the contrast agent or a saline/contrast agent mixture.

An erroneous setting of contrast agent parameters, for example in respect of the flow and/or volume of the contrast agent. The contrast agent parameters are often established beforehand in an injection protocol which controls automatic administration of contrast agent. In this, for example, the flow of contrast agent in ml/s and/or the total volume of the contrast agent to be administered is stipulated, as well as (indirectly conditioned by these two parameters) the time which is provided for the administration of contrast agent. Additionally a maximum pressure limit of the injection pressure can be specified as well as numerous other parameter values. After defining all relevant parameter values the contrast agent administration system executes the administration of contrast agent automatically in line with the injection protocol—therefore if unsuitable parameter values are already set in the injection protocol for the scheduled tomography scan, this has an indirect impact on the resulting image quality of the image data resulting from the tomography scan.

An erroneous positioning of the needle, for example a paravasate positioning, in which the target veins are not correctly hit during an injection, so that little or no contrast agent arrives in the veins.

FIG. 1 shows a sectional image of a human thorax from a contrast-agent-assisted CT scan, in which too much contrast agent has accumulated, whereas FIG. 2 shows a sectional image of the same thorax when sufficient contrast agent has accumulated. It is apparent in FIG. 1 that when too much contrast agent has accumulated the individual organs are displayed with indistinct boundaries, so it is not possible to delineate them sufficiently clearly. In contrast, this delineation is readily possible on the basis of the illustration in FIG. 2.

FIG. 3 shows a sectional image of a thorax from a contrast-agent-assisted CT scan, in which the accumulation of contrast agent in the target structure is insufficient. The result is that at best the spinal column of the patient is dimly identifiable. This sectional image is practically worthless for a diagnosis.

The images from the contrast-agent-assisted scanning procedure are at present either not checked at all or only on the basis of a purely visual inspection of so-called real-time display data or real-time display images. In the context of this application the following basic distinction between image data is made:

Raw image data is data which arises directly during the capture. It hence comprises a collection of detector signals which have not as yet been preprocessed for an image display.

Reconstructed image data is image data which has been derived from the raw image data after a full image reconstruction. It forms the basis for a subsequent diagnosis by medical specialists.

Real-time display data is image data which results from a rough conversion of the raw image data into images and hence in practice can be generated in parallel to the image capture. Real-time display data has a considerably poorer image quality, in particular resolution and quantity of information, than the reconstructed image data according to the above definition. The real-time display data is in particular mostly unfiltered, so that in an extreme case it has strong noise effects as a result of artifacts, etc. It therefore only gives a very simple overview for personnel in situ at the tomography system.

Recording results data is only the raw image data and/or the real-time display data, but not the reconstructed image data. Thus it always involves image data from which a user can draw conclusions about the actual image quality of the image data only with difficulty, if at all.

For a first quality check only the real-time display data is used in the best case and image displays derived therefrom are evaluated roughly by visual inspection. However, an operator can in this case generally only inadequately assess whether a sufficient contrast has been achieved in the image data; in addition there is usually not enough time for a more thorough check. The actual comprehensive reconstruction of the image data usually takes place in the meantime in the background or subsequent to the tomography scan, so that the reconstructed image data is not available until much later. Hence the actual meaningful quality check of the image data does not currently take place until the diagnosis by a diagnostic physician or when using postprocessing applications.

If ultimately the quality of the recording results data was insufficient, this normally means that a diagnosis or an evaluation is not possible with a postprocessing application, or not to the desired extent, since clinically relevant target structures, for instance vessels, are not available in sufficient quality for a diagnosis. These shortcomings are normally not established until a patient, generally speaking an examination object, is no longer present in the immediate vicinity of the tomography system, but for example has already left the radiology department in question. This results in increased extra work in both organizational and financial terms, possibly delays in further diagnosis and not least in an increased radiation dose, if a complete examination has to be repeated completely at a later time.

SUMMARY

At least one embodiment of the present invention, against this backdrop, provides an improved opportunity for how a quality indicator of medical technology recording results data from contrast-agent-assisted tomography scans can be provided. In particular, at least one embodiment relates to providing an opportunity of being able to intervene as early as possible in the event of quality problems, in order if necessary to correct the sequence of the tomography scan.

A control method and a control system are claimed.

Accordingly, in a control method of at least one embodiment, at least one control parameter value is automatically derived from the recording results data in respect of a contrast agent image region during and/or directly after the tomography scan, and represents a quality of the recording results data in the contrast agent image region.

An inventive control system of at least one embodiment comprises at least:
an input interface for the recording results data,
a derivation unit, which in operation during and/or directly after the tomography scan automatically derives at least one control parameter value from the recording results data in respect of a contrast agent image region, which represents a quality of the recording results data in the contrast agent image region. In addition an output interface is preferably provided for forwarding the control parameter value.

Overall a large number of the components for implementing the control system in at least one embodiment of the inventive manner, in particular the derivation unit, can be implemented in whole or in part in the form of software modules on a processor.

At least one embodiment of the invention hence also comprises a computer program product which can be loaded directly into a processor of a programmable image-processing system, with program code segments/modules in order to execute all steps of at least one embodiment of an inventive control method and/or of at least one embodiment of an inventive method for control adjustment if the program product is executed on the control system.

BRIEF DESCRIPTION OF THE DRAWINGS

The invention is explained in greater detail once again below with reference to the attached figures on the basis of example embodiments. In the various figures the same components are provided with identical reference characters. In the figures.

DETAILED DESCRIPTION OF THE EXAMPLE EMBODIMENTS

Figure 1:
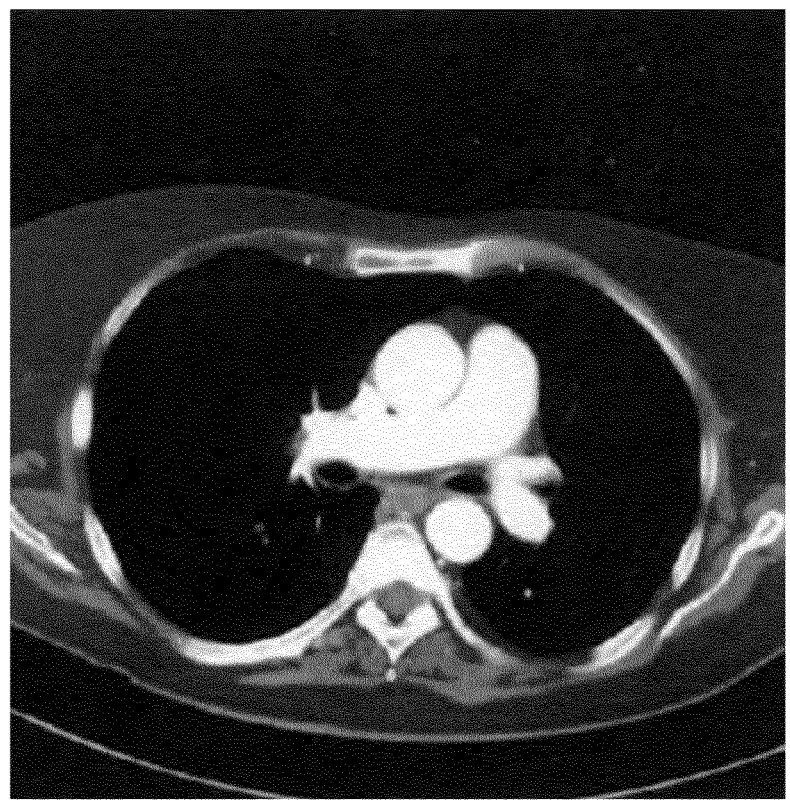
FIG. 1 shows a first sectional image of a human thorax from a contrast-agent-assisted CT scan.

Accordingly, in a control method of at least one embodiment, at least one control parameter value is automatically derived from the recording results data in respect of a contrast agent image region during and/or directly after the tomography scan, and represents a quality of the recording results data in the contrast agent image region.

As already mentioned, the recording results data in particular comprises image data which has not yet undergone a full reconstruction, thus specifically raw image data and/or real-time display data, but also other, "semi-finished" image data, which in its present form cannot be used, at least not yet completely—in other words highly incompletely—for a comprehensive proper diagnosis by a specialist and/or for a comprehensive proper performance of postprocessing steps.

As an examination structure a structure of an examination object (for example of a patient) is defined, which in principle can also include the whole examination object, but is preferably a partial structure thereof. The definition as an "examination" structure ultimately results from the epistemological interest of the specialist subsequently making the diagnosis, i.e. from the information or parameter values which the latter has made available before the performance of the scan in the form of a data request. An examination structure may for example be an organ or a number of organs inside a patient's body, but also bone structures, blood vessels and/or other vascular systems.

The recording results data captured by the examination structure is therefore already analyzed during the tomography scan or directly after it, it being of crucial importance that this analysis is automated, i.e. self-actuating, based on previously defined algorithms or machine-controlled. "Directly after the tomography scan" means that the recording results data is analyzed before transmission as normal to a diagnostician or a postprocessing application or in the presence of a patient or other examination object. In terms of time, an analysis directly after the tomography scan preferably takes place within one hour of the conclusion of the tomography scan.

The analysis is performed on the basis of a predefined control parameter, so that the derived control parameter values can be reproduced and can also be verified subsequently. The control parameter values relate to a contrast agent region, i.e. to such a region within the recording results data which represents an effective region of the examination object, within which an accumulation of contrast agent can be identified or within which normally an accumulation of contrast agent is expected. The control parameter value represents a quality of the recording results data.

In contrast to a purely visual quality check of recording results data, at least one embodiment of the inventive control method thus uses an automated examination based on objective criteria or based on derivation algorithms. As a result it can be ensured that the quality can be identified more effectively, faster and above all more precisely and accurately, which means defective qualities can be identified significantly more reliability. Ultimately a systematic examination takes place without the fully reconstructed image data from the tomography scan being present.

Another aspect of at least one embodiment of the invention is that the performance of the control method takes place in direct temporal proximity or in direct temporal connection with the performance of the tomography scan, which among other things means that it can also be ensured that the examination object is still in situ in the event of a defective quality indicator, in particular is preferably in fact still on a patient couch of the tomography system and in turn is preferably still connected to the contrast agent administration system. In particular in such a case it may be possible to dispense with a repetition of particular scanning processes, in particular the performance of a prescan (topogram scan), a test bolus scan (i.e. the scan after a test injection) or a bolus tracking scan.

A development of at least one embodiment of the invention resides in a method for control adjustment of a contrast-agent-assisted tomography scan sequence of a medical technology tomography system, in which a number of control values for the tomography scan sequence are adjusted as a function of a quality indicator determined in an inventive method and/or of a parameter value derived in the context thereof and/or of examination data used to derive the control parameter value. Thus, at least one embodiment of the inventive control method is performed and based on its results or based on data generated and/or used in the course of the method, fine-tuning of the control of the medical technology tomography system and/or of a contrast agent administration system is subsequently derived for later tomography scans. The interim and/or final results from at least one embodiment of the inventive control method are thus further used to preclude errors, as have perhaps come to light in the context of at least one embodiment of the inventive control method, for the future in the sense of a self-learning system. To this end the interim and/or final results are preferably also recorded and the corresponding protocol is stored, for example archived electronically. Thanks to at least one embodiment of the inventive control adjustment it can be effectively ensured that any errors or problems identified can be counteracted as effectively as possible in future.

An inventive control system of at least one embodiment comprises at least:
- an input interface for the recording results data,
- a derivation unit, which in operation during and/or directly after the tomography scan automatically derives at least one control parameter value from the recording results data in respect of a contrast agent image region, which represents a quality of the recording results data in the contrast agent image region. In addition an output interface is preferably provided for forwarding the control parameter value.

The interfaces mentioned need not necessarily be designed as hardware components, but can also be implemented as software modules, for example if the recording results data can be taken over from another component already implemented on the same device, or has to be transferred to another component only on the basis of software. Likewise the interfaces may consist of hardware and software components, for example a standard hardware interface which is specifically configured by software for the concrete intended use. Additionally, several interfaces can also be combined in one common interface, for example an input-output interface.

Overall a large number of the components for implementing the control system in at least one embodiment of the inventive manner, in particular the derivation unit, can be implemented in whole or in part in the form of software modules on a processor.

At least one embodiment of the invention hence also comprises a computer program product which can be loaded directly into a processor of a programmable image-processing system, with program code segments/modules in order to execute all steps of at least one embodiment of an inventive control method and/or of at least one embodiment of an inventive method for control adjustment if the program product is executed on the control system.

Moreover, at least one embodiment of the invention comprises a tomography system with a recording unit and at least one embodiment of an inventive control system and also a contrast agent administration system with a contrast agent administration control and at least one embodiment of an inventive control system. This differentiation between the tomography system and the contrast agent administration system is therefore relevant, because on the basis of the (interim and/or final) results from at least one embodiment of the inventive control method both a subsequent fine-tuning for the tomography system and for the contrast agent administration system can be derived, as already mentioned above. At least one embodiment of the inventive control system can therefore be implemented as an external module or as a module that is arranged in the tomography system and/or in the contrast agent administration system. As an external module too it can be associated with at least either a tomography system or a contrast agent administration system, so that each of these two systems can also simultaneously comprise at least one embodiment of the inventive control system.

Further particular advantageous embodiments and developments of the invention also emerge from the dependent claims and the following description. In this case the control system can also be developed in accordance with the dependent claims for the control method.

Preferably the control parameter value in at least one embodiment of the inventive control method is derived by the tomography system and/or by a contrast agent administration system. The recording results data thus need not be first forwarded to a data further-processing system for further processing there, but is inventively further processed directly in situ in the tomography system or in the contrast agent administration system. This firstly saves time and secondly ensures that the tomography system or the contrast agent administration system can already start to process the recording results data during the capture or at least directly after it.

The derivation of the control parameter value can for example take place using two variants, which can be used alternatively or additionally to one another: the first variant consists in the control parameter value being derived on the basis of threshold values. A threshold-value-based analysis of the recording results data results with simple means in a control parameter value which ultimately comprises a type of Yes or No statement. The statement thus includes whether a particular quality threshold, represented by the threshold value, has been reached or not. In this case a single threshold value can be defined beforehand or a plurality, preferably two threshold values, on the basis of which an algorithm derives a quality statement in the form of the control parameter value. A lower threshold value can for example comprise a minimum value which should be achieved so that it can be assumed therefrom that sufficient contrast agent has accumulated (cf. FIG. 2). If this threshold value is undershot this would therefore mean that not enough contrast agent has accumulated (cf. FIG. 3). An upper threshold value can comprise a maximum value, which if possible should not be exceeded, since otherwise too much contrast agent will accumulate—as shown in FIG. 1.

For example, a threshold value on which the derivation is based can comprise a minimum radiation value of a contrast agent and/or a minimum absorption value in the region of a significant structure of an examination object. A significant structure in this connection can for example be defined as any structure inside the examination object which is to be examined in greater detail later by a diagnostician as a type of target structure (or examination structure). A significant structure can also comprise another relevant or distinctive (anatomical) structure inside the examination object or even its surrounding area also recorded, from which it is particularly simple to derive whether the image quality in the recording results data is sufficiently high. Thus for example from a minimum radiation value or a minimum absorption value of a structure surrounding the target structure, for example bones, it can where appropriate be easier to derive whether the said values are sufficiently high to state for certain that the image quality in the recording results data is high enough overall. A minimum radiation value or a minimum absorption value in the region of the significant structure can for example be a Hounsfield value. The Hounsfield values are simple to determine in the context of image capture, directly from the raw image data in fact, without also having to perform first further processing steps in the recording results data (for example generation of real-time display data). The procedure according to this first variant is hence particularly simple to perform, effective, fast and nevertheless representative.

If the threshold-value-based method is performed on the basis of Hounsfield values, at least one minimum Hounsfield value, which may differ depending on the type of examination, is defined beforehand as a threshold value. Thus in so-called CTA (Computer Tomographic Angiography—CT Angiography) a different minimum Hounsfield value is defined than in a 3-phase liver examination. The minimum Hounsfield value always in each case represents a sufficient accumulation of contrast agent, and the recording results data is fully or else partially checked for sufficient contrast with the help of an algorithm. In this case the algorithm can check both the achievement of the minimum Hounsfield value and also (optionally) an even distribution of Hounsfield values within the examined recording results data, which for example is particularly relevant in so-called run-off examinations, i.e. examinations of vessels (in the leg) for occlusions, i.e. stenoses.

The second variant is that the control parameter value represents a result of a (preferably automatic) object identification of a significant structure of an examination object. Thus to this end a target-oriented search is performed in the recording results data to see whether a particular significant structure can be identified therein. If such an identification is possible, this in turn means that the quality of the recording results data is sufficient, and in contrast if there is no identification it can be assumed that the quality is insufficient or at least questionable. In contrast to the threshold-value-based method according to the first variant, a target-oriented search is here performed for particular structures inside the examination object, so that these structures can also be identified. This means that this second variant is in many cases more accurate than the first variant and is thus distinguished by being even less prone to errors. With this second variant it is possible to say practically without error whether the recording results data is of a sufficiently high quality, in particular on a target-oriented basis in respect of those structures in the examination object which will subsequently be subject to a diagnosis.

Particularly preferably the object identification here comprises a (particularly preferably automatic) segmentation of the significant structure from surrounding structures of the examination object. Segmentation methods are sufficiently known in the prior art and ultimately result in different structures being distinguished from one another, so that then particular significant structures can be identified therein. For example, a learning-based segmentation algorithm is known from the article Zheng, Yefeng/Georgescu, Bogdan/Ling, Haibin/Zhou, S. Kevin/Scheuering, Michael/Comaniciu, Dorin: "Constrained Marginal Space Learning for Efficient 3D Anatomical Structure Detection in Medical Images", In: Proc. CVPR, 2009, pages 194-201.

With the help of so-called learning-based algorithms anatomical structures can thus be found and segmented inside volume data sets. These algorithms are trimmed in a training procedure to find a wide variety of anatomical structures (e.g. hearts and their functional chambers). If the trained features do not occur inside a volume data set or are encountered, the target structures are not found either. An important and common training feature in CTA data sets is used to identify the contrast agent itself or its distribution in an examination object, i.e. a body or a region of a body. Only if contrast agent has been correctly applied does contrast agent accumulate in vessels or perfused parenchyma. It is precisely these properties which are taken advantage of in the context of the second variant of the invention, to establish whether contrast agent has sufficiently reached particular anatomical regions. For example, the heart and its chambers, including vessels, can only be identified by the contrast agent during segmentation if contrast agent has been correctly applied. If the algorithm is unable to find suitable structures, it can be assumed with a high probability that the image capture was deficient, i.e. the recording results data has quality defects. The user can then be informed immediately after using the segmentation algorithm.

To ensure the results from at least one embodiment of the inventive control method can be controlled and used by a user as well as possible, it is further preferred that on the basis of the quality indicator a signal is emitted to a user if the quality of the recording results data is sufficient and/or unsatisfactory and/or questionable, particularly preferably related to a previously defined purpose of the tomography scan. The user therefore receives qualified information in the form of a sound or light or image or text signal, which enables him immediately and as intuitively as possible to establish whether the tomography scan he performed was ultimately successful. Thus immediately after receipt of the respective signal he can either conclude the scanning procedure (if the scan was successful) and forward the recording results data to corresponding further processing units or repeat the scanning procedure (if the quality of the recording results data is unsatisfactory or questionable) in whole or in part, preferably on the basis of adjusted control values from an inventive control adjustment.

In the context of at least one embodiment of such an inventive method for control adjustment the number of control values for the tomography scan sequence is preferably adjusted such that a parameter value expected according to a simulation and/or preliminary estimation is altered in a follow-up scan scenario, which essentially is designed similarly to a scan scenario, as could be established in the context of at least one embodiment of the inventive control method, so that it represents an improved quality of recording results data. Thus the control adjustment directly aims to improve the quality of the recording results data as much as possible in a follow-up scan at a later time. Comparable scan scenarios are used for this, i.e. a pool of input parameter values is formed which represents such a particular scan scenario. If a tomography scan is performed which has an at least similar pool of input parameter values, the adjusted control parameters are used.

Particularly preferably the number of adjusted control values comprises at least one contrast agent administration control parameter value, which is used for control of automatic contrast agent administration in the context of the tomography scan. The administration of contrast agent is therefore readjusted, so that subsequent contrast-agent-assisted tomography scans are thereby further fine-tuned such that an improved administration of contrast agent is effected to improve the image quality of follow-up scans. Contrast agent administration control parameter values relate in particular to parameter values of the quantity and dosing over time or the composition of the contrast agent. The modification of an injection protocol for automatic administration of contrast agent by altering the contrast agent administration control parameter value in the injection protocol can be regarded as a development of this particularly preferred embodiment. The storage of the altered contrast agent administration parameter values in such an injection protocol ensures that automatically, whenever this injection protocol is used, the new contrast agent administration parameter values are used. To this end it can also be provided that simultaneously several injection protocols are amended on the basis of the final results or interim results of at least one embodiment of the inventive control method.

Figure 2:
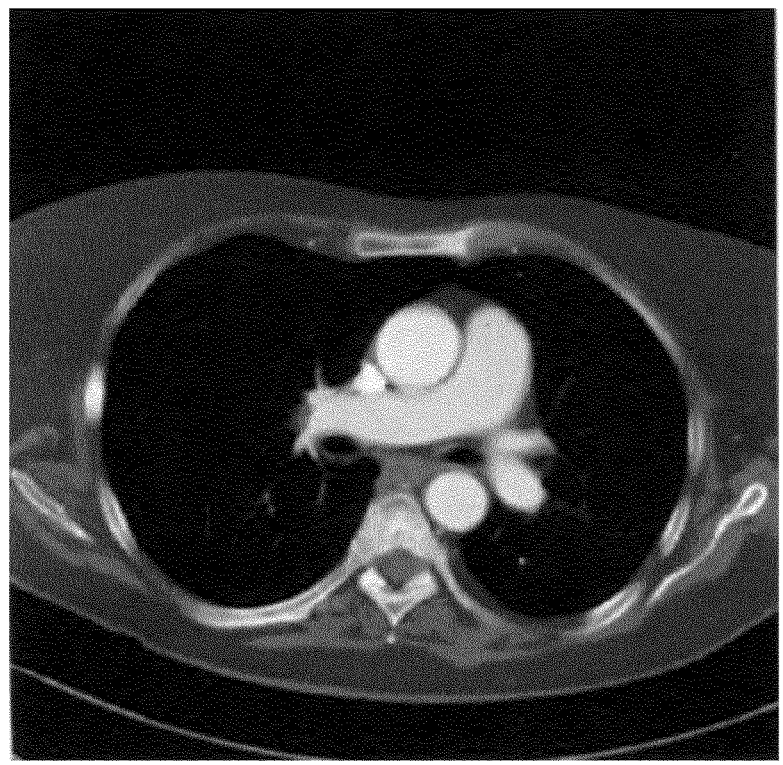
FIG. 2 shows a second sectional image of the same human thorax from a contrast-agent-assisted CT scan.
Figure 3:
FIG. 3 shows a sectional image of a thorax from a contrast-agent-assisted CT scan.

FIGS. 1 to 3 have already been explained above with reference to the problem on which the invention is based.

Figure 4:
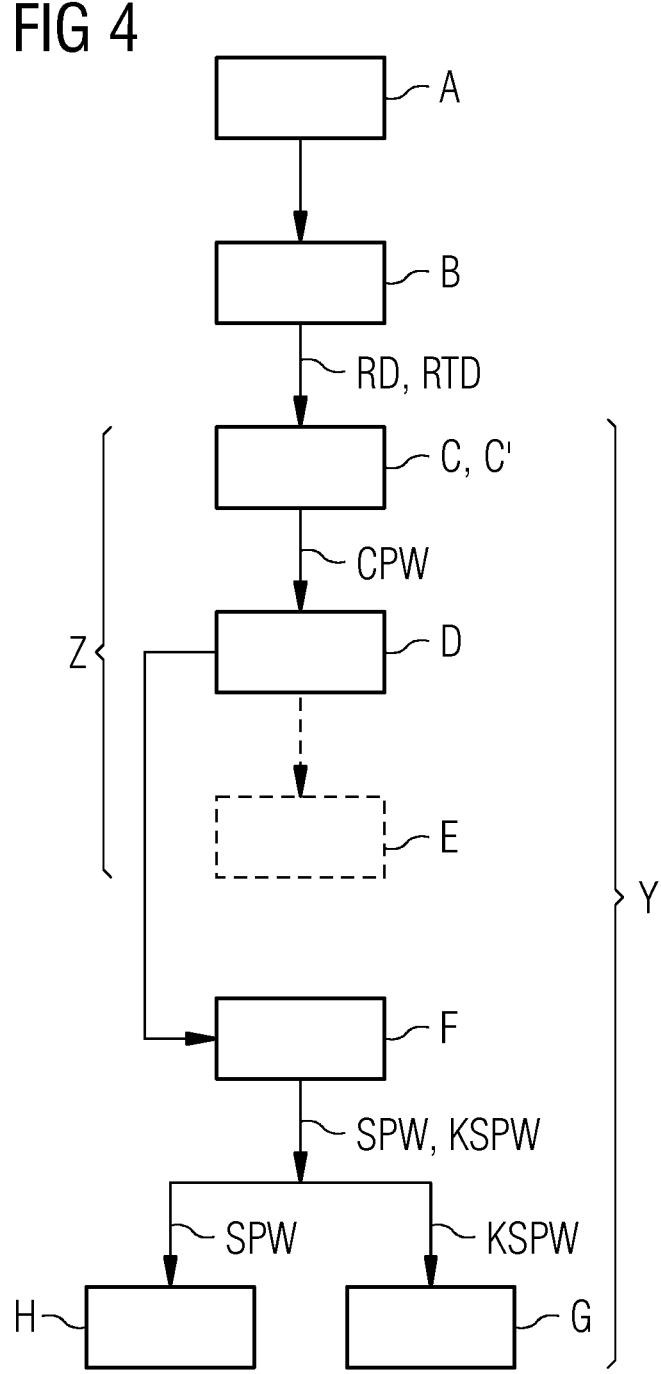
FIG. 4 shows a schematic block diagram of the sequences in the context of an example embodiment of an inventive control method and of an example embodiment of a downstream method for control adjustment.

FIG. 4 shows schematically the sequence of a contrast-agent-assisted tomography scan and of two inventive methods downstream therefrom according to an example embodiment in each case.

In a first step A a contrast agent is injected into an examination object, i.e. a patient, and then in a second step B a tomography scan using a tomography system, for example a computed tomography system, is performed. This results in raw image data RD or if appropriate subsequently real-time display data RTD, which can both respectively also be referred to as recording results data. In two alternatively or additionally usable variants a control parameter value CPW is derived in a third step C, C'—cf. FIGS. 5 and 6—on the basis of the recording results data RD, RTD, and represents a quality of the recording results data RD, RTD. This control parameter value CPW is output via an output interface in a fourth step D and optionally in a fifth step E is converted into a signal which is output to a user.

The steps C, C', D and optionally E are steps in the context of an inventive control method Z. Subsequent to the at least one embodiment of an inventive control method Z an adjustment of control values for the performance of following similar or identical contrast-agent-assisted tomography scans can take place in a step F. Control parameter values SPW and/or contrast agent administration control parameter values KSPW are derived here. The control parameter values SPW are used to adjust a control of the relevant tomography system, i.e. of the tomography system which also performed step B in the previous scan. This adjustment is completed in a step H. Alternatively or additionally an adjustment of injection protocols which are used for the control of a contrast agent administration system can take place in a step G. Using the adjusted contrast agent administration control parameter values KSPW fine-tuned control is again achieved in a subsequent tomography scan with the same contrast agent administration system. The adjustment of the control parameter values SPW or contrast agent administration control parameter values KSPW on the basis of the steps C, C', D, optionally E, F, G, H and/or G thus represents at least one embodiment of a separate inventive control adjustment method Y.

Figure 5:
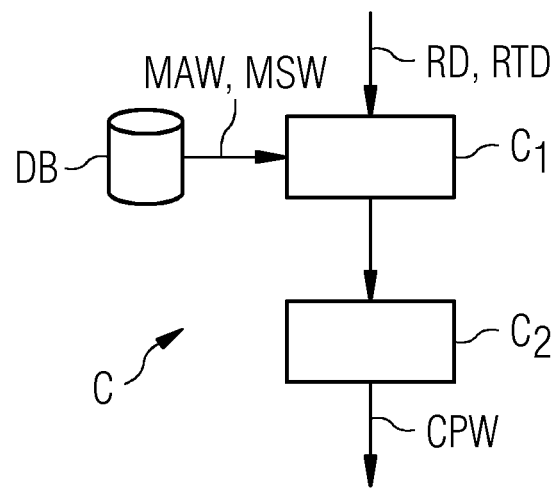
FIG. 5 shows a schematic illustration of a detail of the sequence from FIG. 4 in a first variant.

FIG. 5 shows a first variant of the third step C (see FIG. 4). Here the recording results data RD, RTD is filtered on the basis of threshold values in a first substep $C_1$. To this end a minimum absorption value MAW and/or a minimum radiation value MSW are provided as one or more threshold values from a database DB. The minimum absorption value MAW here represents an absorption of radiation at least to be attained by a significant structure (including the contrast agent stored there), whereas the minimum radiation value MSW represents a minimum irradiation from the region of a significant structure, for instance by storage of contrast agent, in particular tracers.

Both the minimum absorption value MAW and the minimum radiation value MSW thus ultimately represent a threshold, as of which sufficient contrast agent has been stored in the respective significant structure, so that then a sufficient image quality of the recording results data RD, RTD can also be assumed. On the basis of the threshold-value-based filtering in the first substep $C_1$ the control parameter value CPW is generated in a second substep $C_2$, and ultimately indicates whether the quality of the recording results data RD, RTD is sufficient or not.

Figure 6:
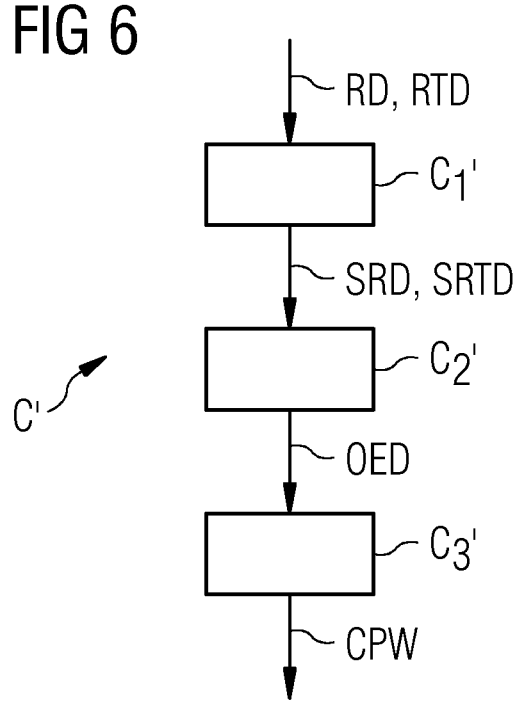
FIG. 6 shows a schematic illustration of a detail of the sequence from FIG. 4 in a second variant and FIG. 7 shows a schematic illustration of an embodiment of an inventive tomography system and of an inventive contrast agent administration system.

FIG. 6 shows in a block diagram the sequence of a second variant of the third step C'. Here in a first substep $C_1'$ a segmentation is performed on the basis of recording results data RD, RTD, on the basis of which individual structures, for example organs, bone structures or vessels inside the examination object, are distinguished from one another. This results in segmented raw image data SRD or segmented real-time display data SRTD, which is then passed to object identification in a second substep $C_2'$. An attempt is thus made to identify a particular structure inside the segmented raw image data SRD or the segmented real-time display data SRTD, in particular such a structure which subsequently, namely during the evaluation of the results of the tomography scan, undergoes a more extensive examination. As a result of the object identification $C_2'$ object identification data OED is generated, on the basis of which in a third substep $C_3'$ the control parameter value CPW is generated, which in turn relates to the quality of the recording results data RD, RTD.

Figure 7:
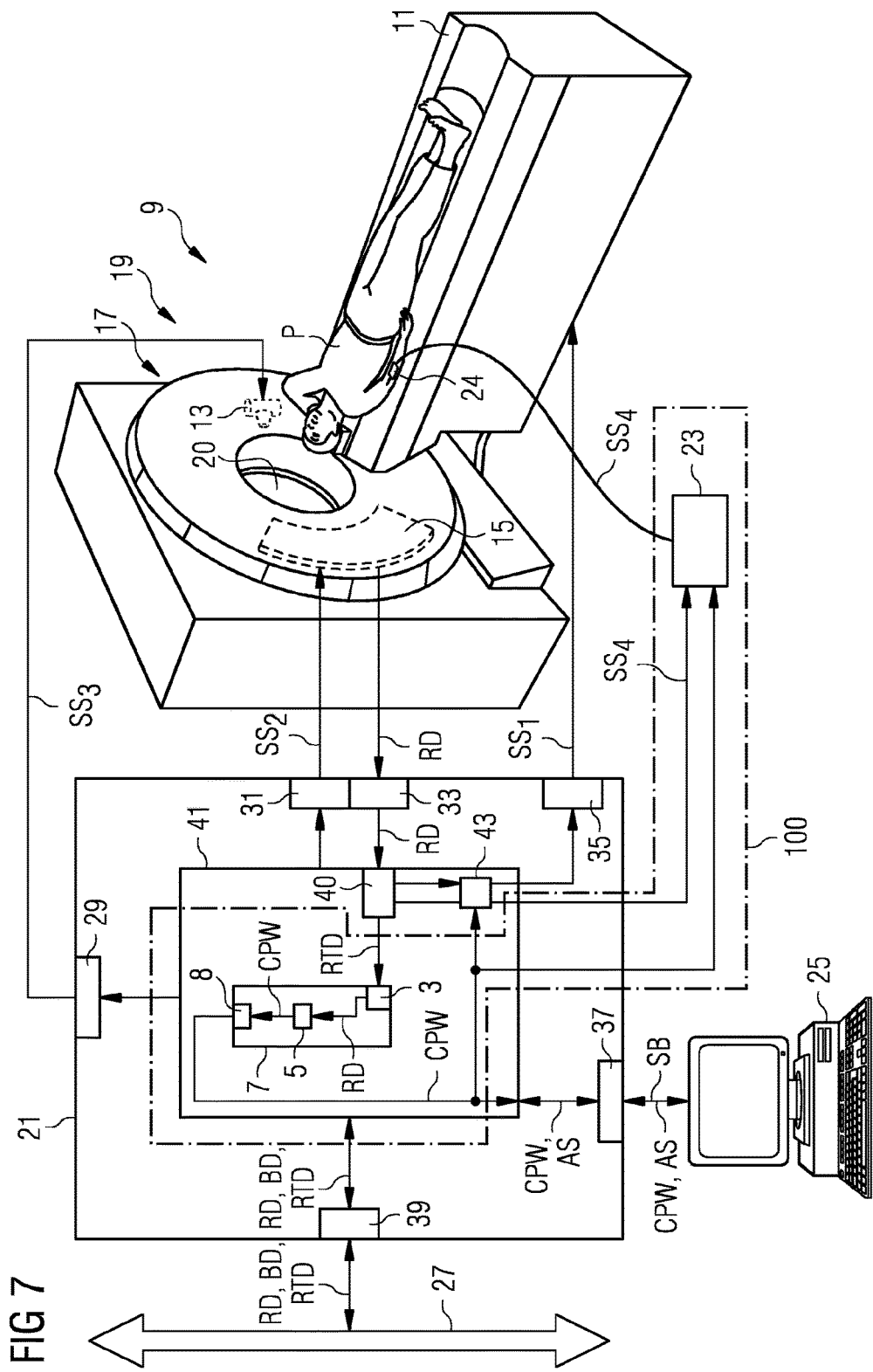

FIG. 7 shows an example embodiment of an inventive tomography system 9, here of a computed tomography system 9, and of at least one embodiment of an inventive contrast agent administration system 100 in an essentially schematic block diagram. The tomography system 9 comprises a central processing unit 21 and a scanner unit 19. The scanner unit 19 comprises a patient table 11 and gantry 17, within which an X-ray source 13 and a detector arrangement 15 can be rotatably attached around an examination region 20. Mounted on the patient table 11 is an examination object P, namely a patient P, which can be introduced into the examination region 20. The patient P is supplied via an injection needle 24 with a contrast agent, for the administration of which a contrast agent administration unit 23 forwards (fourth) control signals $SS_4$ to the injection needle 24.

The central processing unit 21 comprises, in addition to a series of output or input interfaces 29, 31, 33, 35, 37, 39, a control unit 41, within which at least one embodiment of an inventive control system 7 is arranged. Via a first output interface 35 first control signals SS1 are forwarded to the patient table 11, on the basis of which the position of the patient P is varied by moving the patient table 11. A second output interface 31 forwards second control signals $SS_2$ to the detector unit 15, on the basis of which the detector unit 15 is controlled during the capture of raw image data RD. Via a third output interface 29 third control signals SS3 are forwarded to the X-ray source 13, on the basis of which the X-ray source 13 emits X-ray radiation on a controlled basis. An input interface 33 receives the raw image data RD from the detector unit 15. Via a first input and output interface 37 signals CPW, AS, namely control parameter values CPW and alarm signals AS, are forwarded to a computer terminal 25 for display or further processing. Control instructions SB to the central processing unit 21 can also be entered into the computer terminal 25. A second input and output interface 39 is used to enter the raw image data RD, and if appropriate image data BD preprocessed (i.e. reconstructed) by the real-time display data RTD, into a patient data archiving system 27.

Arranged in the control unit 41 are, apart from the control system 7, an image preprocessing unit 40 and a control signal generation unit 43. The control system 7 comprises an input interface 3 for receiving the recording results data RD, RTD, a derivation unit 5 and an output interface 8.

In a contrast-agent-assisted tomography scan a contrast agent is introduced via the injection needle 24 into the body of the patient P with the help of the contrast agent administration unit 23. This corresponds to step A according to FIG. 4. Then on the basis of the first control signals SS1 the patient P is introduced into the examination region 20 and, on the basis of the second control signals $SS_2$ and the third control signals $SS_3$ to the X-ray source 13 or to the detector unit 15, a scanning procedure according to step B in FIG. 4 is performed. The resulting raw image data RD passes via the first input interface 33 into the central processing unit 21, where it is forwarded to the control unit 41—more specifically into the image processing unit 40. There so-called real-time display data RTD can be derived from the raw image data RD. The raw image data RD and/or the real-time display data RTD is then fed via the input interface 3 of the control system 7 into the same and is examined there in the processing unit 5.

This examination corresponds to the alternative or complementary steps C, C' according to FIG. 4 (or FIG. 5 or 6). Hence the result of the processing is a control parameter value CPW which is forwarded via the output interface 8 of the control system 7 to further units within the central processing unit 21 and also to outside the central processing unit 21: the control parameter value CPW is namely forwarded via the first input and output interface 37 to the computer terminal 25 and if appropriate an alarm signal AS is additionally generated, that for example alerts a user if a requisite image quality in interpretation of the control parameter value has not been achieved. A user who receives such an alarm signal AS can then repeat the scanning procedure or administration of contrast agent and take necessary steps to increase the image quality. To increase the future image quality the parameter values CPW can also be forwarded to the control signal generation unit 43, which therefrom derives a fine-tuning of control parameter values for a tomography scan or contrast agent administration control parameter values for control of the contrast agent administration system 100. Thus as a result the adjustment of the control parameter values SPW or contrast agent administration control parameter values KSPW explained on the basis of steps F, H, G (FIG. 4) can be performed.

The control system 7 is in the present case spatially associated with the tomography system 9, but it can also be interpreted as part of the contrast agent administration system 100, which therefore comprises the contrast agent administration unit 23 and the control system 7.

Finally, it is pointed out once again that the method described in detail above and the apparatuses illustrated are merely example embodiments which can be modified in a variety of ways by the person skilled in the art, without departing from the scope of the invention. Furthermore, the use of the indefinite article 'a' or 'an' does not exclude the possibility that the relevant features may also be present multiple times.

The invention claimed is:

1. A control method for determining a quality indicator of medical technology recording results data from a contrast-agent-assisted tomography scan of an examination structure via a tomography system, the method comprising:
   automatically deriving, at least one of during and directly after the tomography scan, at least one control parameter value from the recording results data in respect of a contrast agent image region, the at least one control parameter value representing a quality of the recording results data in the contrast agent image region.

2. The control method of claim 1, wherein the at least one control parameter value is derived by at least one of the tomography system and a contrast agent administration system.

3. The control method of claim 1, wherein the at least one control parameter value is derived on the basis of thresholds.

4. The control method of claim 3, wherein a threshold value, on which the derivation is based, comprises at least one of a minimum radiation value of a contrast agent and a minimum absorption value in the region of a significant structure of an examination object.

5. The control method of claim 1, wherein the at least one control parameter value represents a result of an object identification of a significant structure of an examination object.

6. The control method of claim 5, wherein the object identification comprises a segmentation of the significant structure of surrounding structures of the examination object.

7. The control method of claim 1, wherein on the basis of the quality indicator a signal is emitted to a user if the quality of the recording results data is at least one of sufficient, unsatisfactory and questionable.

8. The control method of claim 7, wherein on the basis of the quality indicator a signal is emitted to a user if the quality of the recording results data is at least one of sufficient, unsatisfactory and questionable, related to a previously defined purpose of the tomography scan.

9. A method for control adjustment of a contrast-agent-assisted tomography scan sequence of a medical technology tomography system, the method comprising:
   adjusting a number of control values for the tomography scan sequence as a function of a quality indicator at least one of
      determined in the control method of claim 1,
      a control parameter value derived in the context thereof, and
      examination data used to derive the control parameter values.

10. The method of claim 9, wherein the number of control values for the tomography scan sequence is adjusted such that a parameter value, to be expected according to at least one of a simulation and preliminary estimation, is altered in a follow-up scan scenario, essentially designed similarly to a scan scenario, as could be established in the context of the control method of claim 1, such that it represents an improved quality of recording results data.

11. The method of claim 10, wherein the number of adjusted control values comprises at least one contrast agent administration control parameter value, used for control of automatic contrast agent administration in the context of the tomography scan.

12. The method of claim 11, wherein an injection protocol for the automatic contrast agent administration is modified by adjusting the contrast agent administration control parameter value in the injection protocol.

13. A non-transitory computer program product, loadable directly into a processor of a programmable control system, including program code segments to execute the control method of claim 9 when the program product is executed on the control system.

14. A non-transitory computer readable medium including program code segments for, when executed on a control device of a radar system, causing the control device of the radar system to implement the method of claim 9.

15. A non-transitory computer program product, loadable directly into a processor of a programmable control system, including program code segments to execute the control method of claim 1 when the program product is executed on the control system.

16. A non-transitory computer readable medium including program code segments for, when executed on a control system, causing the control system to implement the method of claim 1.

17. The control method of claim 1, wherein the recording results data is image data which has not yet undergone a full reconstruction.

18. A control system for determining a quality indicator of medical technology recording results data from a contrast-agent-assisted tomography scan of an examination structure using a tomography system, the control system comprising:
   memory storing computer-readable instructions; and
   one or more processors configured to execute the computer-readable instructions such that the one or more processors are configured to perform operations including,
   recording results data; and
   deriving, at least one of during and directly after the tomography scan, at least one control parameter value from the recording results data in respect of a contrast agent image region, the at least one control parameter value representing a quality of the recording results data in the contrast agent image region.

19. A tomography system, comprising:
   an image recorder; and
   the control system of claim 18.

20. A contrast agent administration system, comprising:
   instructions configured to control administration of a contrast agent to a patient; and
   the control system of claim 18.

* * * * *